United States Patent
Park et al.

(10) Patent No.: US 11,358,980 B2
(45) Date of Patent: Jun. 14, 2022

(54) METHOD FOR EFFICIENT PRODUCTION OF PSICOSE

(71) Applicant: SAMYANG CORPORATION, Seoul (KR)

(72) Inventors: Ji Won Park, Suwon-si (KR); Sung Won Park, Yongin-si (KR); Chong Jin Park, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 189 days.

(21) Appl. No.: 16/463,977

(22) PCT Filed: Nov. 24, 2017

(86) PCT No.: PCT/KR2017/013542
§ 371 (c)(1),
(2) Date: May 24, 2019

(87) PCT Pub. No.: WO2018/105934
PCT Pub. Date: Jun. 14, 2018

(65) Prior Publication Data
US 2020/0377540 A1    Dec. 3, 2020

(30) Foreign Application Priority Data

Dec. 8, 2016 (KR) .................. 10-2016-0167048

(51) Int. Cl.
| | | |
|---|---|---|
| *C07H 3/02* | (2006.01) | |
| *C07H 1/06* | (2006.01) | |
| *B01D 15/18* | (2006.01) | |
| *B01D 15/36* | (2006.01) | |

(52) U.S. Cl.
CPC .............. *C07H 3/02* (2013.01); *B01D 15/185* (2013.01); *B01D 15/361* (2013.01); *C07H 1/06* (2013.01)

(58) Field of Classification Search
None
See application file for complete search history.

(56) References Cited

U.S. PATENT DOCUMENTS

| | | | |
|---|---|---|---|
| 2,985,589 | A | 5/1961 | Broughton et al. |
| 2016/0138053 | A1 | 5/2016 | Yang et al. |
| 2017/0313734 | A1 | 11/2017 | Kim et al. |

FOREIGN PATENT DOCUMENTS

| | | |
|---|---|---|
| CN | 102946961 | 2/2013 |
| CN | 105431541 | 3/2016 |
| CN | 108474014 | 8/2018 |
| JP | 4627841 | 2/2011 |
| JP | 2011-206054 | 10/2011 |
| JP | 2019-536822 | 12/2019 |
| JP | 2020-500556 | 1/2020 |
| KR | 10-2009-0104983 | 10/2009 |
| KR | 10-0967093 | 7/2010 |
| KR | 10-2011-0108185 | 10/2011 |
| KR | 10-1318422 | 10/2013 |
| KR | 10-2014-0021974 | 2/2014 |
| KR | 10-2014-0054997 | 5/2014 |
| KR | 10-2014-0080282 | 6/2014 |
| KR | 10-2016-0046143 | 4/2016 |
| KR | 10-2016-0062349 | 6/2016 |
| TW | 201619177 | 6/2016 |
| WO | 2011-121181 | 10/2011 |
| WO | 2013-177058 | 11/2013 |
| WO | 2014-158558 | 10/2014 |

OTHER PUBLICATIONS

N. Wagner et al., "Model-based cost optimization of a reaction-separation integrated process for the enzymatic production of the rare sugar d-psicose at elevated temperatures", Chemical Engineering Science, 2015, vol. 137, p. 423-435.
Integration of biocatalysis and simulated moving bed chromatography for the high-yield production of rare sugars Author: Wagner, Nina Doctoral Thesis, ETH Zurich, CH doi:10.3929/ethz-a-010346995, XP055512035.
N. Wagner et al., "Multi-objective optimization for the economic production of d-psicose using simulated moving bed chromatography", Journal of Chromatography A, 2015, vol. 1398, p. 47-56.
EPO, Supplementary European Search Report of EP 17877905.4 dated Jun. 30, 2020.
Park, Jong-Uk et al., "Construction of Heat-Inducible Expression Vector of Corynebacterium glutamicum and C. ammoniagenes: Fusion of λ Operator with Promoters Isolated from C. ammoniagenes", J. Microbiol. Biotechnol., 2008, vol. 18, No. 4, pp. 639-647.
Nguyen Van Duc Long et al., "Separation of D-psicose and D-fructose using simulated moving bed chromatography", J. Sep. Sci., 2009, vol. 32, pp. 1987-1995.
Wagner, Nina, "Integration of biocatalysis and simulated moving bed chromatography for the high-yield production of rare sugars", Doctor of Science of Eth Zurich, 2014.
Wagner, Nina, "Integration of biocatalysis and simulated moving bed chromatography for the high-yield production of rare sugars", Doctoral Thesis of Swiss Federal Institute of Technology Zurich, 2014.
SIPO, Office Action of CN 201780075573.2 dated Jan. 6, 2022.

*Primary Examiner* — Traviss C McIntosh, III
(74) *Attorney, Agent, or Firm* — Lex IP Meister, PLLC

(57) ABSTRACT

The present invention relates to a method for effectively utilizing fructose raffinate obtained in the process for separating psicose conversion product with a high purity chromatography in the process for preparing psicose, and more specifically, it is utilized for preparation of fructose-containing raw material solution for preparation of psicose by putting fructose raffinate obtained in the process for preparing psicose into the process for preparing fructose.

12 Claims, 2 Drawing Sheets

[Fig. 1]
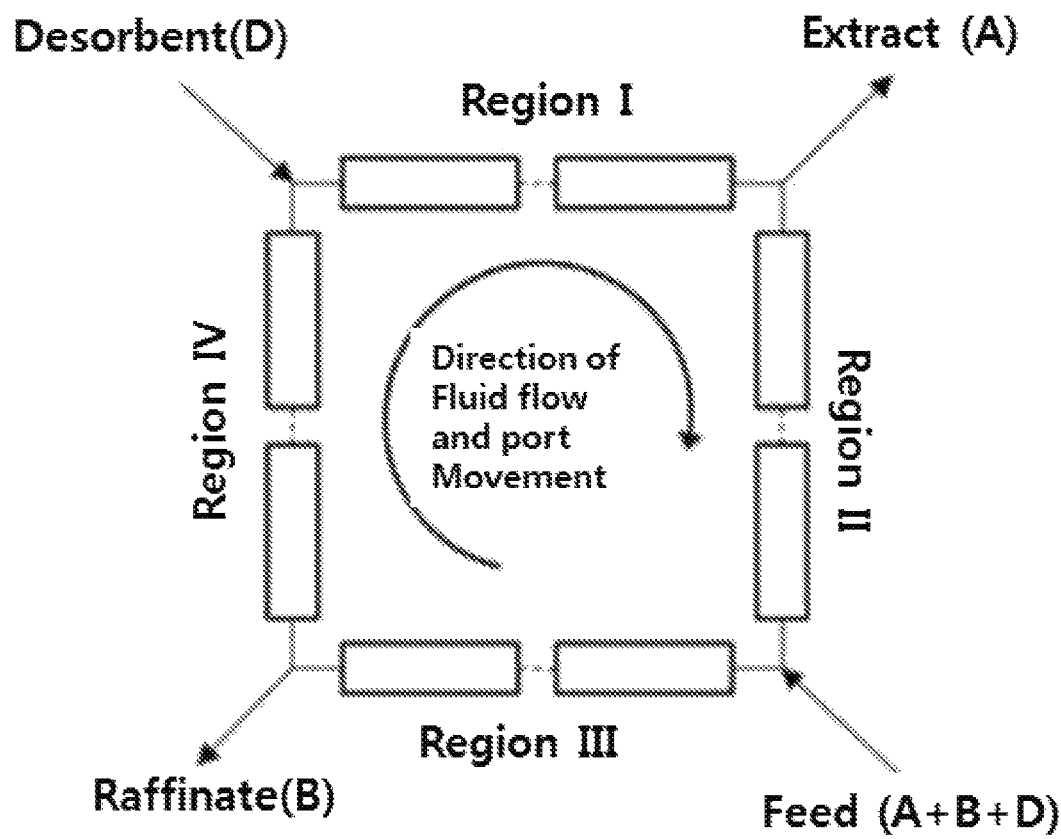

[Fig. 2]
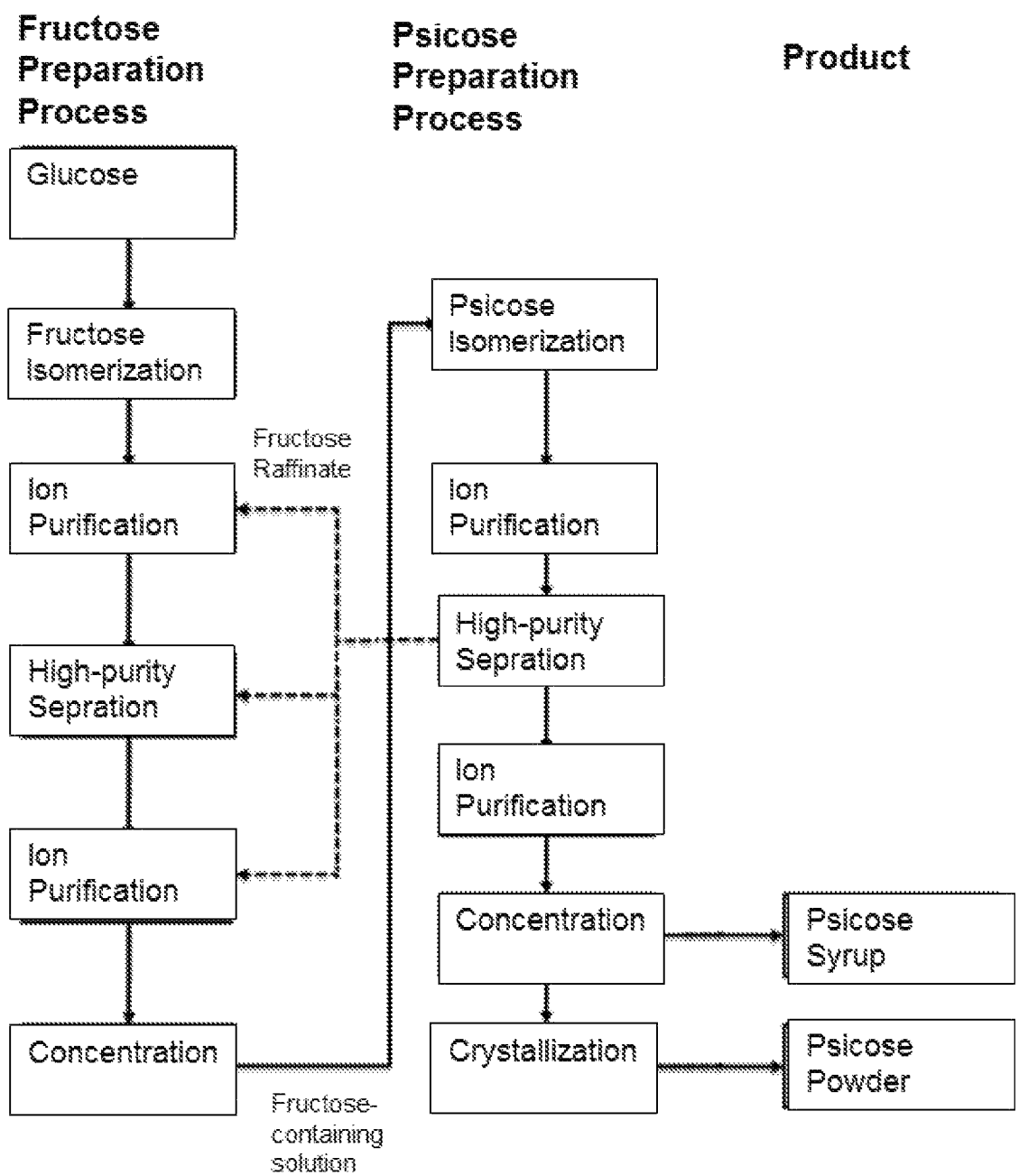

METHOD FOR EFFICIENT PRODUCTION OF PSICOSE

TECHNICAL FIELD

The present invention relates to a method for effectively utilizing fructose raffinate obtained in psicose preparation process, and more specifically, the fructose raffinate obtained in the psicose preparation process is utilized for preparing psicose as fructose-containing raw material, by putting fructose raffinate obtained in the psicose preparation process into the fructose preparation process.

BACKGROUND ART

Psicose is an epimer of fructose (D-fructose) and is one kind of functional saccharides known as a rare saccharide, and it has been known to have an effect on prevention and improvement of diabetes, since it has sweetness of about 60 to 70% of sugar and almost zero calorie. In addition, psicose is known to have excellent solubility, and it is one of materials where utilization for food is attracting attention.

There are a chemical method and a biological method in the method for preparing psicose, and recently, a method for preparing psicose with a biological method performs psicose conversion reaction by contacting fructose-containing substrate solution with a psicose epimerase or a microorganism producing the enzyme.

The reaction raw material used for the psicose conversion process may be fructose isomerization reactant obtained by isomerization reaction of glucose obtained from degradation of starch, etc.

However, it is required to separate psicose with high purity, since the reaction solution comprising D-psicose is low purity product. In fact, various methods have been applied to separate industrially produced materials with high purity, and in case of sugar, a product is produced by crystallization after making high purity solution mainly by using a chromatography. To obtain a high purity psicose product from the psicose conversion reaction solution, a high purity separation process may be carried out, and in addition, to obtain psicose crystals, a psicose crystallization process may be carried out by using a high purity of psicose syrup.

Since not only psicose but also fructose fraction comprising fructose at a high concentration are obtained as raffinate in the psicose separation process, a method for enhancing the purity and yield of psicose and increasing the availability of raw material by recycling the fructose raffinate is required.

DISCLOSURE

Technical Problem

One example of the present invention is to provide a method for preparing psicose by putting fructose raffinate obtained in the pscioce preparation process into the separation process of fructose preparation, to prepare fructose-containing raw material and putting it as raw material for preparing psicose in the psicose preparation processed, and an apparatus used for that, in order to enhance the purity and yield of psicose and increase the availability of raw material by utilizing fructose raffinate.

Another example of the present invention is to provide a method for preparing fructose-containing raw material by putting fructose raffinate of psicose preparation process into the separation process of fructose preparation and an apparatus used for that, in order to enhance the purity and yield of psicose and increase the availability of raw material by recycling fructose raffinate.

Technical Solution

An embodiment of the present invention relates to a method and an apparatus for preparing psicose comprising preparing a fructose-containing raw material by putting a fructose raffinate obtained in the separation process of psicose preparation into the separation process of fructose preparation and putting the prepared fructose-containing raw material as a raw material for psicose preparation process. The method for preparing fructose-containing raw material being useful for psicose preparation according to the present invention is a method of enhancing the purity and yield of psicose and increasing the availability of raw material by recycling the fructose raffinate.

In the method of preparation of psicose according to the present invention, since the fructose raffinate with fructose at a high concentration is obtained in the separation process of psicose preparation, the method for preparing psicose using a fructose-containing raw material obtained from a fructose raffinate in the separation process of psicose preparation which is put into the separation process of fructose preparation and then is obtained as fructose-containing raw material for psicose preparation, is a process utilizing the fructose preparation process for the psicose preparation process.

An embodiment of the present invention relates to a method of preparing psicose, comprising steps of separating psicose-conversion product with a simulated moving bed (SMB) chromatography to obtain psicose fraction and fructose raffinate, and recycling the fructose raffinate as a raw material of psicose conversion reaction.

An additional embodiment of the present invention relates to a method of preparing a fructose-containing raw material for psicose preparation by separating psicose-conversion products with a simulated moving bed (SMB) chromatography to obtain psicose fraction and fructose raffinate, and putting the fructose raffinate into a fructose preparation process, for example, fructose separation process.

Another embodiment of the present invention relates to an apparatus of preparing psicose comprising a psicose conversion reactor for performing psciocse conversion reaction using fructose-containing raw material with using a biological catalyst, a SMB chromatography separator which comprises a column packed with cation exchange resin having an active group, a feed inlet and an outlet for discharging psicose fraction and fructose raffinate, and a fructose separation device for separating fructose from the fructose raffinate discharged from the chromatograph separator.

The apparatus of preparing psicose may further comprise a connecting part for connect a fructose preparation device and a psicose preparation device, in order to provide the fructose-containing raw material obtained from the fructose separator or a fructose preparation device, for providing the fructose-containing raw material discharged from the concentrator of the fructose preparation apparatus, into the psicose preparation device. In addition, the apparatus of preparing psicose may optionally comprise a storage tank for storing the fructose-containing raw material, to control the feed amount and the feed rate of the fructose-containing raw material being put into the psicose conversion reactor.

Hereinafter, the present invention will be described in more detail.

The method for preparing the fructose-containing raw material to be used for the psicose conversion reaction according to the present invention is a method for preparing the fructose-containing raw material by obtaining the psicose fraction and fructose raffinate in step of separating the psicose conversion product with the SMB chromatography and putting the fructose raffinate into the separation process of fructose preparation.

In one specific embodiment, the method for preparing the fructose-containing raw material comprises (1) a psicose conversion step of preparing psicose-conversion product with a fructose-containing raw material; (2) a psicose separation step of obtaining psicose fraction and fructose raffinate by performing ion purification and separation with a SMB chromatography of the psicose conversion product; and (3) a step of preparing the fructose-containing raw material by putting the fructose raffinate into the separation process of fructose preparation.

The method for preparing psicose according to the present invention may comprise steps of separating psicose-conversion product with SMB chromatography to obtain psicose fraction and fructose raffinate, putting the fructose raffinate into the separation process of fructose preparation to prepare fructose-containing raw material, and conducting psicose conversion reaction for the fructose-containing raw material.

In one specific embodiment, the method of preparing psicose comprises (1) a psicose conversion step of preparing psicose-conversion product with a fructose-containing raw material; (2) a psicose separation step of obtaining psicose fraction and fructose raffinate by performing ion purification and separation with SMB chromatography of the psicose-conversion product; (3) a step of preparing the fructose-containing raw material by putting the fructose raffinate into the separation process of fructose preparation and (4) a step of putting the fructose-containing raw material into the psicose conversion process. The method of preparing psicose may further comprise (5) a psicose crystallization step of ion purification, concentration and crystallization of the psicose fraction obtained in the separation process of psicose preparation.

The process of preparation of psicose of the present invention may use both continuous and batch processes, preferably a continuous process.

In the present specification, the term "raffinate" is also called as "residual solution". The products obtained from as a separation process which is provided by a feeding material include two fraction of a target fraction including a target material to increase its content by the separation process and a residual solution including a material to be removed or to reduce its content. In one embodiment of the present invention, the product obtained in the psicose conversion process is a mixture of fructose as a raw material and psicose as a product material. After the psicose conversion product is passed through the SMB chromatograph separation, the psicose fraction with increased content of psicose and the residual solution are produced. The fructose raffinate can be obtained, since fructose used as a reacting raw material is included at a large amount in the residual solution.

The present invention is advantageous in effective method of preparing psicose using the fructose raffinate, the high yield of fructose preparation process by obtaining the fructose-containing raw material from the fructose preparation process with the fructose raffinate and then providing the psicose conversion process as a raw material, and the process design and operation because the fructose raffinate is treated by using the fructose preparation process, resulting in no additional treatment device required for the fructose raffinate.

Hereinafter, the process of psicose preparation including the recycling of fructose raffinate obtained in the high purity separation process for the psicose conversion product according to the present invention will be described in detail by each step.

(1) Psicose Conversion Process

The psicose conversion process is a process for obtaining psicose from the fructose-containing raw material by performing a psicose conversion reaction, and produces a reaction solution including psicose as reaction product converted from fructose.

In one specific embodiment of the present invention, the method for preparing psicose according to a biological method may culture a strain producing psicose epimerase or a recombinant strain including a gene encoding the psicose epimerase and may react the psicose epimerase with a fructose-containing raw material to produce psicose. The psicose epimerase reaction may be performed in a liquid phase reaction or a solid phase using an immobilization enzyme.

Otherwise, psicose may be produced by obtaining a strain producing psicose epimerase or a recombinant strain including a gene encoding the psicose epimerase, and reacting the fructose-containing raw material with a composition for psicose preparation comprising one or more selected from the group consisting of microbial cell of the strain, culture of the strain, lysate of the strain, and extract of the lysate or culture. When psicose is prepared by using the microbial cell of strain producing the psicose epimerase, it may be performed with a liquid phase reaction or a solid phase using an immobilized microbial cell.

In one specific embodiment of the present invention, the strain producing the psicose epimerase may be the strain which has high stability and can convert fructose to psicose at a high yield or produce the psicose epimerase. The strain may be a strain isolated from nature or its mutant strain, non-GMO strain, or a recombinant strain in which a gene encoding the psicose epimerase is introduced. In one embodiment of the present invention, various known strains as the non-GMO strain may be used. The recombinant strain may be prepared by using various host cells, for example, *E. coli*, *Bacillus* sp. strain, *Salmonella* sp. strain and *Corynebacterium* sp. strain, etc, but preferably, GRAS strain such as *Corynebacterium* sp. Strain, and may be *Corynebacterium glutaricum*.

The psicose conversion process according to the one embodiment of the present invention is performed by a biological method. For example, in case of solid phase reaction, it may further include a step of packing immobilizede psicose epimerase or microbial cell on a support into a column and a step of providing fructose solution into the packed column. The column being packed by the support-immobilized enzyme or microbial cell and the packing method may be performed according to easily selecting appropriate one by one skilled in the technical field where the present invention belongs according to the used enzyme or microbial cell, or immobilization carrier. In one specific embodiment of the present invention, a packed-bed column may be prepared by packing the immobilized enzyme or microbial cell into a column. An enzymatic reaction, that is, the conversion of fructose to psicose may be performed by providing a substrate of fructose solution to the packed-bed column.

In the conversion reaction of psicose, the reaction may be performed under the condition of pH 4.5 to 7.5, for example, pH 4.7 to 7.0, or pH 5.0 to 6.0 or pH 5.0 to 5.5. In addition, the reaction may be performed under the temperature condition of 30° C. or higher, for example 40° C. or higher. The enzyme activity for converting fructose to psicose (for example, epimerase) can be controlled by a metal ion, and therefore in the production of psicose, the conversion efficiency from fructose to psicose, in the production rate of psicose can be increased, when the metal ion is added. Thus, the composition for producing psicose may further comprise one or more of metal ions selected from the group consisting of copper ion, manganese ion, calcium ion, magnesium ion, zinc ion, nickel ion, cobalt ion, iron ion, aluminum ion, etc.

The detailed technical contents regarding psicose and its preparation method are disclosed in Korean patent publication No. 2014-0021974, Korean patent publication No. 2014-0054997, Korean patent publication No. 2014-0080282, or Korean patent No. 10-1318422.

The fructose as a raw material put into the psicose conversion process according to the present invention may be prepared by a biological method or chemical method, preferably by a biological method. The fructose as a raw material may be provided as a liquid phase raw material, or a powdery raw material such as fructose powder, and in case of fructose syrup, it may be the product obtained in the biological method or chemical preparation method, or one prepared by dissolving fructose powder in a solvent such as water.

In an embodiment of preparing the fructose raw material with a biological method, the fructose may be obtained by performing a fructose isomerization process which isomerizes a glucose-containing raw material with a fructose isomerase or a microbial cell producing the enzyme and separating it through the primary ion purification, high purity chromatography separation process, the secondary ion purification and concentration for the products of fructose isomerization process.

In the method for producing psicose, for effective production of psicose, the concentration of fructose used as a substrate may be 85 w/v % or higher, 90 w/v % or higher, or 95 w/v % or higher, for example, 85 to 99 w/v %, 88 to 99 w/v %, 88 to 99 w/v %, 85 to 87% (w/v), 88 to 90% (w/v), 91 to 93% (w/v), 94 to 99% (w/v) or 97 to 99% (w/v), based on the total reactants. The concentration of fructose may be decided by considering economics of process and solubility of fructose, and the fructose may be used as a solution prepared by dissolving fructose in a buffer solution or water (for example, distilled water).

To illustrate the fructose preparation process according to an example of the present invention, the fructose may be obtained from sugar or glucose. As a result, a method for preparing psicose at high yield by using generalized and inexpensive raw material such as glucose, fructose and sugar is provided, thereby enabling mass production of psicose.

To illustrate one embodiment of fructose preparation process of the present invention, the saccharification solution with 88% by weight or higher of glucose content is obtained by enzymatic hydrolysis, after mixing corn starch with water to be 30 to 35% by weight. Then, by passing a step of removing impurities of the saccharification solution and a fructose isomerization step, a fructose syrup with 40 to 44% by weight of fructose content is obtained. Then, glucose raffinate and fructose fraction are obtained by using a SMB chromatography and are passed through the secondary ion purification and concentration of the fructose fraction are performed, to produce n a fructose-containing solution with 85% by weight or higher, for example 85 to 99% by weight of fructose content. The SMB adsorption separation method is described in the following (2) item. The process for removing impurities may be performed by a step for removing insoluble materials, a step of decoloring by using activated carbon, and a step of passing solution into an ion exchange resin column for removing impurities of colored components and ion components, etc.

A specific embodiment of fructose separation process may comprise the primary ion purification, a high purity chromatography separation, secondary ion purification, a concentration and a crystallization, and optionally carry out desalting, decoloring, or decoloring and desalting process of conversion product.

The concentration step included in the fructose preparation process of the present invention may be conducted with various methods, so as to be fructose content of 85% by weight or higher. For example, the fructose fraction obtained by the SMB adsorption separation method (for example, solid concentration of 20~30%) may be concentrated to be the solid concentration of 45 to 55% by weight through the concentration process.

(2) Separation Process of Psicose-Conversion Product

The psicose preparation method according to the present invention may comprise a separation process of psicose-conversion product, including ion purification and SMB chromatography separation of the psicose-conversion product. In one specific embodiment, SMB chromatography separation to the psicose-conversion product is performed, thereby producing psicose fraction with higher psicose content than the psicose-conversion product and fructose raffinate. The psicose fraction is put into a concentration step or crystallization step and the fructose raffinate is put into a fructose preparation process and recycled.

The psicose fraction may be performed in separation/purification so that the psicose content is 85% by weight or higher, for example, 85% by weight to 95% (w/w). The fructose content of fructose raffinate obtained in the high purity separation process may be 85% by weight or higher, for example 85% by weight to 98% by weight. The content of saccharides including disaccharides or higher degree of polymerization other than fructose and glucose in the fructose raffinate may be preferably less than 10% by weight based on the solid content of the total saccharides. The saccharides including disaccharides or higher degree of polymerization in impurities include maltose, isomaltose and etc., and may contain maltose-related or isomaltose-related oligosaccharides.

When the fructose raffinate is reused, the content of impurities is increased as the numbers of recycle are increased. It is preferable to perform the process so that the content of impurities of the fructose raffinate is adjusted below the specific numerical range. When the content of impurities is over the specific numerical range, the impurities are removed by discharging the fructose raffinate partially or overall in the psicose preparation process. For example, it is preferable to maintain the content of saccharides including disaccharides or higher degree of polymerization in the fructose raffinate to less than 10% by weight, for example, less than 8% by weight, less than 6% by weight or lower than 5% by weight, based on 100% by weight of the total saccharide solid of fructose raffinate.

The ion purification step in the psicose preparation process is a process for removing ion comprised in psicose-conversion product, and it may be conducted before and/or after SMB chromatography separation step. The primary ion purification which performs ion purification process before conducting the SMB chromatography separation may be carried out by the same or different method with the following secondary ion purification of psicose fraction. For example, it may be performed by using 1, 2 or more separation columns packed with same kind or different kinds of ion exchange resin. The ion purification process may be performed at 35 to 50° C. temperature, for example, 38 to 58° C., considering physical properties of resin used for ion purification and ion purification efficiency.

In one embodiment of the present invention, before performing the primary ion purification process of psicose-conversion product, a process for treating the psicose-conversion product with activated carbon may be further carried out optionally.

In one embodiment of the present invention, the high purity separation step using SMB chromatography is a separation method useful for securing stability of materials, due to no phase change in the separation process. In these adsorption separation methods, a chromatography separation method has been used in abundance as a liquid phase adsorption separation method. Among them, a simulated moving bed (SMB) adsorption separation method is a separation technology proposed in U.S. Pat. No. 2,985,589 in 1961, and has an advantage that the purity and productivity are excellent and the use of less solvent is possible, compared to the conventional batch chromatography, by continuous separation using many of columns. The simulated moving bed (SMB) adsorption separation process is a process, in which injection of separation target mixture and production of raffinate and extract are implemented continuously.

The fundamental principle of SMB is to copy the flow of immobilized or moving counter-current and enable the continuous separation by moving positions between columns at regular intervals. The material which moves fast due to its weak affinity with an adsorbent moves in the direction of flow of liquid phase and collects in the extract, and the material which moves slowly due to its strong affinity with an adsorbent moves in the direction of flow of immobilized phase and collects in raffinate. Columns are connected continuously, and the inlet consists of mixture and moving phase, and the outlet consists of target extract and raffinate.

Since a cation exchange resin of strong acid in which a salt is added, which is widely used for a process of monosaccharide separation is used as a separation resin in the SMB, metal ions are comprised in products obtained after performing the separation process. An example of cation exchange resin of strong acid may be a cation exchange resin in which a calcium activated group is attached.

FIG. 1 shows a process chart of general simulated moving bed (SMB) adsorption separation apparatus. The general simulated moving bed (SMB) adsorption separation apparatus consists of adsorbent inlet port positioned in 4 sections consisting of one or more columns and between each section, an extract discharge port that is a strong absorbate, a separation target mixture (feed) inlet port and a raffinate discharge port that is a weak adsorbate. The separation method of mixture using similar simulated moving bed (SMB) adsorption separation apparatus may be applied for separation of mixture of aromatic hydrocarbons, separation process of ethyl benzene, separation process of chiral compounds, etc, and it may be applied for separation process of racemic mixture drugs which are final products or intermediates in the drug preparation process.

The high purity separation process may be performed at 45 to 70° C. temperature, for example 50 to 65° C.

(3) Input of Fructose Raffinate into Fructose Preparation Process

A fructose-containing raw material is prepared by putting the fructose raffinate obtained in the high purity chromatography separation process of psicose preparation according to the present invention, and psicose is prepared by providing the prepared fructose-containing raw material as a raw material of psicose preparation process.

The fructose raffinate obtained in the psicose preparation process is recycled and used as a reaction raw material, thereby increasing the production yield of psicose to maximum and reducing the production cost of psicose. In addition, since the fructose raffinate obtained in the psicose preparation process is treated by using a fructose preparation process, thereby not requiring an additional treatment apparatus, it is advantageous in the view of process design and operation. By operating psicose preparation process, in order to continuously produce target products such as psicose, a bioreactor may be operated with maintaining the appropriate level of productivity compared to the primary activity.

In one embodiment of the present invention, so that the fructose raffinate obtained in the high purity separation process of psicose preparation meets the proper conditions to be used as a raw material of psicose conversion reaction, one or more kinds of processes selected from the group consisting of ion purification, high purity separation process (e.g. SMB separation) and concentration process may be further performed, and the processes may be carried out by using a fructose preparation apparatus by putting into the separation process of fructose preparation.

When the fructose separation process is performed by recycling the fructose raffinate obtained in the psicose preparation process with the separation process of fructose preparation according to one embodiment of the present invention, in the SMB chromatography separation process performed in the fructose preparation process, the process with recycle of fructose raffinate has increased yield of solid separation of fructose fraction compared to the process without recycle of fructose raffinate, and for example, the process with recycle of fructose raffinate has the solid separation yield of fructose fraction of 50 to 80% by weight based on 100% by weight of solid of raw material put into SMB separation process.

In specific one embodiment, the fructose raffinate may be put and recycled into one or more kinds of processes selected from the group consisting of the primary ion purification, separation using SMB chromatography and the secondary ion purification which are separation processes of fructose preparation. Preferably, in order that the fructose raffinate passes through the high purity separation process using SMB chromatography to maintain the content of glucose and impurities including disaccharides or higher degree of polymerization other than fructose obtained in the fructose raffinate to be lower than a specific content, fructose raffinate may be put in the high purity separation process using SMB chromatography or its previous process, and for example, it may be put into the primary ion purification or high purity separation process using SMB chromatography. When putting the fructose raffinate into the primary ion purification or high purity separation process, the concentration of the impurities is reduced, because impurities including glucose and disaccharides or higher degree of polymerization except fructose can be removed in the high purity separation process of fructose preparation.

When the content of impurities in the fructose raffinate is over a specific numerical range, they may be discharged and removed in the psicose preparation process. For example, it is preferable to maintain the content of saccharides including disaccharides or higher degree of polymerization in the fructose raffinate to less than 10% by weight, for example, less than 8% by weight, less than 6% by weight, or less than 5% by weight, based on the 100% by weight of the total saccharides of fructose raffinate. The saccharides including disaccharides or higher degree of polymerization among the impurities include maltose, isomaltose, etc, and may include maltose or isomaltose related oligosaccharides.

Since the increased calcium content of the fructose raffinate contains decreases the activity of psicose conversion reaction, a process for controlling the calcium ion concentration can be performed additionally, or the secondary ion purification process after the SMB separation process in the separation process of fructose preparation may be performed. Thus, t the calcium concentration of the fructose-containing raw material which passed through the separation process of fructose preparation may be controlled at a concentration ranges of 0.05 mM, or lower, 0.01 mM or lower, 0.005 mM or lower, or 0.001 mM or lower.

The fructose raffinate obtained in the chromatography separation process has the electrical conductivity of 20 to 200 μs/cm, and the proper range of electrical conductivity may be reached by treating the fructose raffinate with ion purification process, and the fructose-containing raw material of the treated product may have the electrical conductivity of 0 to 15 μs/cm.

For recycling the fructose raffinate obtained in the SMB chromatography process of psicose preparation as a raw material of psicose conversion reaction, when the calcium (Ca) ion mixed in the SMB chromatography process is not purified, the activity of enzyme or microbial cell may be decreased, and therefore it may negatively affect the production of psicose.

The metal ion such as calcium affecting the psicose conversion reaction negatively may be removed by using a chromatography packed with ion exchange resin. Specifically, an ion exchange step is performed by using strong basic or weak basic anion resin substituted with a hydroxyl group (OH—) being capable of combine with the metal ion.

The ion purification performed in the separation process of fructose preparation may be performed by the same method with the ion purification conducted in the separation process of psicose-conversion product of the (2) item.

The fructose raffinate obtained in the high purity separation process of psicose preparation is 15 to 25 Brix. By considering that the fructose-containing raw material provided in the psicose conversion process is 45-55 Brix, for example, about 50 Brix, it is preferable to increase the content of fructose by performing a concentration process. The concentration process in the fructose preparation process may comprise concentration under the temperature of 70 to 85° C. for 10 to 15 min, as fructose has higher thermal stability than psicose.

In one embodiment of the present invention, when the fructose raffinate obtained in the high purity separation process of psicose preparation is put into the separation process of fructose preparation, the mixing ratio with fructose isomerization product may be properly regulated in order to maximize the utilization of fructose raffinate. Considering the aspect of recycle of fructose raffinate, it is preferable to set the mixing ratio to maximally utilize the fructose raffinate obtained in the high purity separation process. For example, the fructose raffinate provided into the separation process of fructose preparation may increase mixing amount of the fructose raffinate up to the fructose content to a specific numerical value or higher, to maintain the yield and concentration of the final fructose-containing raw material in the fructose preparation process. If necessary, the input amount of fructose raffinate may be properly controlled by considering the mixing ratio with the fructose isomerization product of fructose preparation process, and may equip a storage tank for fructose raffinate.

For example, when the fructose raffinate is put into the primary ion purification process of fructose preparation, it may be mixed with fructose isomerization product and treated. When the fructose raffinate is put into SMB separation process, it may be mixed with the primary ion purified products and treated. When the fructose raffinate is put into the secondary ion purification process, it may be mixed with the fructose fraction of SMB separation process and treated.

In the present invention, when the fructose raffinate and fructose solution are equally adjusted to 50 Brix, the mixing ratio of fructose raffinate (fructose solution:fructose raffinate) put into the fructose preparation process and fructose solution as the product of isomerization in the fructose preparation process, may be fructose solution 65 to 95% by weight and fructose raffinate 5 to 35% by weight, preferably, fructose solution 75 to 92% by weight and fructose raffinate 8 to 25% by weight, for example, fructose solution 80 to 90% by weight and fructose raffinate 10 to 20% by weight, based on 100% by weight of the total content of fructose solution and fructose raffinate.

In one embodiment of the present invention, a process for preparing fructose from sugar or glucose is exemplified and described, and the fructose preparation process may comprise (A) a fructose isomerization process which prepares fructose isomerization product by performing a fructose isomerization reaction with sugar or glucose-containing raw materials; (B) a fructose separation process which performs the primary ion purification and separation using a SMB chromatography of the fructose isomerization product to obtain fructose fraction and glucose raffinate; and (C) a process of ion purification and concentration of the fructose fraction.

The fructose preparation process of the present invention may use both continuous and batch processes, preferably a continuous process. Hereinafter, the fructose preparation process through fructose raffinate recycle according to the present invention will be described in detail by each step.

In one embodiment of the present invention, when preparing fructose by isomerizing glucose, fructose may be obtained by isomerizing a glucose-containing raw material. The fructose isomerization process is a step of obtaining fructose by hydrolyzing sugar or isomerizing glucose as a raw material for preparing fructose.

The enzyme used for hydrolysis may be one or more kinds selected from the group consisting of β-D-fructosidase including β-fructofuranosidase, invertase, saccharase, etc, sucrase, α-glucosidase and α-D-glucohydrolase, but not limited thereto. The enzyme for isomerizing glucose may be glucose isomerase or phosphoglucoisomerase, but not limited thereto.

In one embodiment of the present invention, in order to separate and concentrate the fructose isomerization product, the primary ion purification and SMB chromatography separation process of the fructose isomerization product obtained in the step (A) may be performed. The separation process of fructose preparation may be conducted by the same method, process and reaction conditions with the common fructose preparation processes. The primary ion purification and SMB chromatography are substantially same as described in the separation process of psicose conversion product of (2) item.

The separation process of fructose preparation may comprise the primary ion purification, SMB chromatography separation, the secondary ion purification and concentration, and optionally, the process for removing impurities in fructose isomerization product may be performed by a step for removing insoluble materials, a step of decoloring by using activated carbon, and a step of passing solution into a ion exchange resin column for removing impurities of colored components and ion components, etc. After passing through the process for removing impurities of fructose isomerization product, the fructose syrup with fructose solid content of 40 to 44% by weight is obtained.

Then, glucose raffinate and fructose fraction may be obtained by using a simulated moving bed (SMB) adsorption separation method, and a fructose solution with the solid content of 45 to 55% by weight based on 100% by weight of the total solid content may be obtained by performing the secondary ion purification and concentration of fructose fraction.

For separation of glucose and fructose, it may be performed substantially same as SMB chromatography separation process used in the (2) separation process of psicose conversion product, and for example, a calcium (Ca) type strongly-acidic cation resin having the particle size of 220~320 μm may be used. The fructose preparation process of the present invention may use both continuous and batch processes, preferably a continuous process. Hereinafter, the fructose preparation process through fructose raffinate recycle according to the present invention will be described in detail by each step.

For separation of glucose and fructose, it may be performed substantially same as SMB chromatography separation process used in the (2) separation process of psicose conversion product, and for example, a calcium (Ca) type strong acidic cation resin having the particle size of 220~320 μm may be used. The high purity separation process may be performed at the temperature of 40 to 60° C., for example at 60° C.

As the primary ion purification method, it may be carried out by the same or different method with the primary ion purification of psicose fraction, and for example, it may be performed by using 1, 2 or more separation columns packed with same kind or different kinds of ion exchange resin. The ion purification process may be performed by setting process conditions considering physical properties of resin used for ion purification and ion purification efficiency.

The process for removing impurities may be performed by a process for removing insoluble materials, and a process of decoloring by using activated carbon, and passing solution into a column in which ion exchange resin for removing impurities of colored components and ion components, etc. is packed.

A fructose raw material having desired fructose content may be prepared by performing the secondary ion purification and concentration process of the fructose fraction obtained in the high purity separation process.

The concentration process comprised in the fructose preparation process of the present invention makes the fructose content 85% by weight or higher by concentration by various methods. For example, the fructose fraction obtained by the simulated moving bed adsorption separation method (for example, solid concentration 20~30%) may be concentrated up to the solid concentration of 45 to 55% by weight through the concentration process. The concentration process in the fructose preparation process may comprise concentration under the temperature of 70 to 85° C. for 10 to 15 min. The concentration may concentrate it under decompressed or vacuumed conditions by using a falling film evaporator or thin film evaporator. The concentration process in the fructose preparation process may comprise concentration under the temperature of 70 to 85° C. for 10 to 15 min.

(4) Input of Fructose-Containing Raw Material into Psicose Conversion Reaction

The final product obtained in the fructose preparation process according to the present invention is put into the psicose preparation process as a reaction raw material for psicose conversion reaction.

The fructose content of fructose isomerization product in the fructose preparation process may be 40 to 44% by weight, and the fructose content of fructose fraction obtained through the high purity separation process may be 85% by weight or higher, and the fructose content of the final product obtained through the concentration process may be 85 to 99% by weight. The fructose raw material put into the psicose conversion reaction may have the fructose content of 85% by weight or higher, for example 85% by weight to 99% by weight and glucose content of 10% by weight or lower, for example 1% by weight to 10% by weight.

As one embodiment of the present invention, when the fructose content of fructose-containing raw material solution is 88% by weight, the fructose content of psicose conversion product may have the fructose content of 64 to 67% by weight and the psicose content of 21 to 24% by weight and the glucose content of 8 to 10% by weight. In addition, when the fructose content of fructose-containing raw material solution is 95% by weight, the fructose content of psicose conversion product may have the fructose content of 68 to 71% by weight and the psicose content of 24 to 27% by weight and the glucose content of 2 to 5% by weight.

The fructose content comprised in the fructose raffinate may be 85% by weight or higher, for example, 85% by weight to 99% by weight. When the fructose raffinate obtained in the separation process in the psicose preparation process is recycled to the fructose preparation process, it is a method for reducing production load of fructose raw material effectively compared to the case of no recycle.

The psicose fraction obtained in the separation process of psicose preparation process of the present invention may be commercialized as syrup which is a liquid phase through a psicose concentration process, or may be commercialized as psicose crystals through a psicose crystallization process.

(5) Psicose Concentration or Crystallization Process

The psicose fraction obtained in the high-purity separation process using SMB chromatography in the psicose preparation process of the present invention may be commercialized as liquid phase syrup through a psicose concentration process, or may be commercialized as psicose crystals through a psicose crystallization process.

It is a step of preparing concentrates obtained by ion purifying and concentrating psicose fraction obtained in the SMB chromatography separation of the step (2). The concentrates may be used as a psicose syrup product or prepared for psicose crystals by putting into a crystallization process.

In one embodiment of the present invention, the secondary ion purification of psicose fraction obtained in the high purity separation process using SMB chromatography may be performed, and it may be performed by the same or different methods with the primary ion purification performed in the separation process.

The psicose content in the psicose solution for collecting psicose crystals should be contained at a high concentration in the supersaturation condition, but the psicose content of psicose conversion product is low, so direct crystallization for psicose conversion product cannot be conducted and a process of purification and concentration up to the desired level should be performed to increase the psicose content before the crystallization step.

In one specific embodiment of the present invention, the step of concentrating purified psicose solution may be performed at 55 to 75° C. When the temperature of concentrated solution is increased over 75° C., thermal modification of D-psicose may occur, and when decreased less than 55° C., desired level of concentration is difficult to achieve. Since the temperature of product is rapidly increased by evaporation heat as the concentration progresses, it should be concentrated rapidly by maintaining the temperature of concentrated solution to 75 or less.

In one specific embodiment of the present invention, in order to achieve thermal modification of psicose and desired level of concentration, it may be concentrated in the range of 55 to 75° C. temperature, preferably 60 to 70° C. The concentration process may be conducted once or twice or more repeatedly until achieving the desired concentration level.

Specifically, the concentration process of psicose fraction obtained in the SMB chromatography separation process may be performed by various methods, and the solid content in the concentrates may be 70 Brix or higher. For example, the psicose fraction obtained by the SMB adsorption separation method (for example, solid content 20~30% by weight) may be concentrated to the solid content of 70 Brix or higher through the concentration process. The solid content in the psicose concentrates may be 70 Brix or higher, for example, 70 Brix to 85 Brix.

The concentration process in the psicose preparation process may comprise concentrating in the temperature range of 55 to 75° C. for 10 to 15 min. The concentration may concentrate under decompressed or vacuumed conditions by using a falling film evaporator or thin film evaporator.

The psicose content comprised in the psicose concentrates is almost same as psicose content of psicose fraction obtained in the SMB chromatography separation process, and the solid content is increased, thereby enabling the crystallization process to perform. The psicose content comprised in the psicose concentrates may be 94% by weight or higher, 95% by weight or higher, 96% by weight or higher, 97% by weight or higher, 98% by weight or higher, or 99% by weight or higher, based 100% by weight of the solid total content.

The psicose crystallization process comprises a step of secondary ion purification of psicose fraction obtained in the high-purity separation, a step of concentrating the ion-purified psicose fraction, and a step of obtaining psicose crystals and psicose crystallization mother liquor by crystallizing psicose from the concentrates. A specific example of the psicose separation process may include the primary ion purification, high-purity chromatography separation, the secondary ion purification, concentration and crystallization processes, and optionally, may carry out desalting process, decoloring or decoloring and desalting process of psicose conversion product.

It may comprise separation/purification so that the content of psicose in the psicose fraction is 85% by weight or higher, 90% by weight or higher, 91% by weight or higher, 92% by weight or higher, 93% by weight or higher, 94% by weight or higher, or 95% by weight or higher, for example, 85% by weight to 99.9% (w/w).

The psicose purity contained in the psicose crystals may be 90% by weight or higher, 95% by weight or higher, or 99% by weight or higher, and the psicose content in the crystallization mother liquor may be 85% by weight or higher, 90% by weight or higher, 93% by weight or higher, or 95% by weight or higher, for example, 85% by weight to 95% by weight.

The psicose collected by the method of the present invention may be purified and/or crystallized by common methods, and these purification and crystallization belong to common technologies to one skilled in the art. For example, it may be implemented by one or more methods selected from the group consisting of centrifugation, filtration, crystallization, ion exchange chromatography and combinations thereof.

In one embodiment, the secondary ion purification may be conducted for the psicose fraction obtained in the high purity separation process using SMB chromatography, and it may be carried out by the same or different methods with the primary ion purification used in the separation process of psicose.

The method for preparing D-psicose crystals according to the present invention may comprise a step of concentrating purified D-psicose solution. The content of psicose in the psicose solution for collecting psicose crystals should be 70% by weight or higher. The purity of psicose in the psicose solution prepared by the psicose epimerase is low as 20 to 30% by weight, so direct crystallization cannot be conducted and a process of purification and concentration up to the desired level should be performed to increase the content of psicose before the crystallization step. In one specific embodiment of the present invention, in order to achieve thermal modification of psicose and desired level of concentration, the concentration may be implemented in the temperature range of 55 to 75° C. The concentration process may be conducted once or twice or more repeatedly until achieving the desired concentration level.

The step of crystallization by cooling may comprise inducing crystal growth by repeatedly conducting temperature rising and cooling, after rapidly cooling in the temperature range of 10 to 25° C. through a heat exchanger.

The method for preparing D-psicose crystals according to the present invention may further comprise a step of drying after recovering psicose crystals collected in the crystallization step by centrifugation and washing it with deionized water.

One embodiment according to the present invention relates to an apparatus of preparation of psicose comprising a psicose conversion reactor for performing psciocse conversion reaction from fructose-containing raw material by using a biological catalyst, a simulated moving bed (SMB) chromatography separator which comprises a column packed with cation exchange resin having an active group, a feed inlet and an outlet for discharging psicose fraction and fructose raffinate, and a fructose separation device for separating fructose from the fructose raffinate discharged from the separator.

The apparatus of preparation may further equip a heat exchanger for cooling of fructose raffinate, and may further comprise a storage tank storing the fructose-containing raw material before being put into the psicose conversion reactor.

The fructose separation device may comprise an ion purifier equipped with a column packed with ion exchange resin which ion purifies fructose isomerization product, and a column packed with cation exchange resin in which an active group is attached, and may comprise a simulated moving bed (smb) chromatograph separator which is equipped with an inlet into which product passed through the ion purifier is put and an outlet for discharging psicose fraction and fructose raffinate, a concentrator for concentrating the fructose fraction discharged from the separator, and a connecting part for connecting a fructose preparation device for providing the fructose-containing raw material discharged from the concentrator into the psicose preparation device and a psicose preparation device.

Effect of the Invention

The process of preparing psicose of the present invention is preparing psicose by putting fructose raw material obtained in the process for preparing fructose into the process of converting psicose and preparing fructose raw material by putting fructose raffinate obtained in the process for separating psicose into the process for preparing fructose, and it provides a method for enhancing the purity and yield of psicose and increasing the availability of raw material.

BRIEF DESCRIPTION OF DRAWINGS

FIG. 1 is a diagram showing one example of general SMB process.

FIG. 2 is schematized one example of a series of process for preparing psicose which is preparing fructose-containing raw material solution by putting fructose raffinate obtained in the step of high purity separation among the process for preparing psicose into the fructose isomerization process and is conducting the psicose conversion reaction by using thereof, according to one example of the present invention.

DETAILED DESCRIPTION OF THE EMBODIMENTS

Hereinafter, the present invention will be described in more detail with the following examples. However, these examples are only for illustrative purpose, and the scope of the present invention is not limited by these examples.

Preparative Example 1. Preparation of Psicose Syrup

A psicose syrup was prepared from a fructose substrate by the biological method substantially same with the preparation method disclosed in the Korean laid-open patent publication No. 2014-0054997.

Specifically, the encoding gene of psicose epimerase derived from *Clostridium scindens* (*Clostridium scindens* ATCC 35704) (DPE gene; Gene bank: EDS06411.1) was introduced into a recombinant vector (pCES_sodCDPE), and *Corynebacterium glutaricum* was transformed by using the prepared recombinant vector (pCES_sodCDPE) plasmid with electroporation. A bead including the transformed *Corynebacterium glutaricum* cell was prepared and packed into an immobilization reaction column, and a psicose syrup was prepared from 40 brix of 88% by weight of fructose or 95% by weight of fructose. That is, the psicose syrup of 21~23 (w/w) % of which solid mixture weight ratio of glucose:fructose:psicose:oligosaccharide is 41:39:15:5 from 88% by weight of fructose-containing substrate (psicose syrup A), and the psicose syrup of 24~26 (w/w) % of which glucose:fructose:psicose:oligosaccharide=6:67:25:2 from the raw material comprising 95% by weight of fructose content (psicose syrup B).

Preparative Example 2. Preparation of Fructose Raffinate

Two kinds of psicose syrups obtained from Preparative Example 1 were flew through the column at a room temperature which was packed with resin in which cation exchange resin, anion exchange resin and cation and anion exchange resin mixed resin at a rate of twice the volume of ion exchange resin per hour and desalted in order to remove impurities such as colored and ion components, etc.

Then, after separating high purity of psicose fraction by using a chromatography packed with calcium ($Ca^{2+}$) type of ion exchange resin, the remainder was collected as raffinate. The raffinate collected from the psicose syrup obtained from the raw material of 77% by weight of fructose content (psicose syrup A) included 85 to 98% by weight of fructose, 1 to 10% by weight of glucose, and 1 to 5% by weight of reducing sugar.

The raffinate collected from the psicose syrup obtained from the raw material of 95% by weight of fructose content (psicose syrup B) included 88 to 98% by weight of fructose, 1 to 8% by weight of glucose, and 1 to 4% by weight of reducing sugar.

Example 1. Production of Psicose Using Fructose Raffinate

To produce 10 tons of solids of 95% by weight of psicose content by using the fructose-containing raw material solution of 88% by weight of fructose content obtained in Preparative Example 2, the psicose conversion process and separation process were carried out at flow rate 3.8 $m^3$/hr. The psicose content of product collected through the psicose conversion process was 20 to 23% by weight, and they passed through the separation process at a concentration of 45 to 50% by weight after ion purification. The raffinate which was generated when separated by using Ca+ type separation (SMB) resin was generated by 3 $m^3$ per hour.

Specifically, in the preparation process of fructose, after mixing corn starch with water so as to be 30 to 35% by weight, enzymatic hydrolysis was progressed to collect saccharification liquid of 88% by weight or higher of glucose content. Then, the saccharification liquid was under vacuum drum filtration and insoluble materials were removed, thereby obtaining fructose isomerization product (fructose content 42% by weight syrup).

The fructose raffinate of psicose preparation process obtained in Preparative Example 2 was concentrated to 88% by weight of fructose content and 50% by weight of the total solids (50 Brix) and mixed with the product which passed through the fructose isomerization process (fructose content 42% by weight syrup), and put into the ion purification process consisting of strongly acidic resin, weakly basic resin and strongly acidic and weakly basic mixed resin. That is, by adjusting the total solid content of fructose isomerization product and fructose raffinate put into the primary ion purification process to 50% by weight (50 Brix), the mixture ratio of the fructose isomerization product and fructose raffinate of Preparative Example 2 was 8:2 to 9:1 of weight ratio. After the mixed fructose syrup massed through the primary ion purification and was concentrated to the total solid 50% by weight, it passed through the SMB chromatography process. The glucose raffinate and fructose fraction were obtained by performing the SMB process and the fructose-containing solution of 88% by weight of fructose content was obtained by performing the secondary ion purification and concentration process. To the fructose-containing solution, the psicose conversion reaction and separation process were carried out with the method substantially same as Preparative Example 1.

The process was carried out, repeated 10 times, and the mixture substrate and the composition of saccharides of raffinate by each recycle were analyzed and shown in the following Table 1. The mixture solution shown in the following Table 1 means the fructose-containing raw material obtained after putting the fructose raffinate obtained from the separation process of psicose preparation into the separation process of fructose preparation.

cation liquid of 88% by weight or higher of glucose content. Then, the saccharification liquid was under vacuum drum filtration and insoluble materials were removed, thereby obtaining fructose isomerization product (fructose content 42% by weight syrup).

The fructose raffinate of psicose preparation process obtained in Preparative Example 2 was concentrated to 88% by weight of fructose content and 50% by weight of the total solids (50 Brix) and mixed with the product which passed through the fructose isomerization process (fructose content 42% by weight syrup), and put into the ion purification

TABLE 1

| Classification | Saccharides including disaccharides or higher degree of polymerization | Glucose | Fructose | Psicose | Reducing sugar | Psicose yield |
|---|---|---|---|---|---|---|
| F95 raw material | 1.1% | 5.0% | 88.1% | 0.0% | 5.8% | 22.9% |
| raffinate | 1.5% | 8.3% | 85.6% | 0.3% | 4.3% | |
| 1st mixture solution | 1.1% | 5.0% | 88.2% | 0.0% | 5.7% | 22.9% |
| 1st raffinate | 1.5% | 8.3% | 85.5% | 0.4% | 4.3% | |
| 5th mixture solution | 1.3% | 4.9% | 88.2% | 0.0% | 5.6% | 22.9% |
| 5th raffinate | 1.5% | 8.3% | 85.4% | 0.4% | 4.3% | |
| 10th mixture solution | 1.3% | 4.8% | 88.3% | 0.0% | 5.8% | 22.9% |
| 10th raffinate | 1.5% | 8.3% | 85.1% | 0.4% | 4.3% | |

As can be seen in the Table 1, it was demonstrated that the fructose purity of raw material put into the psicose conversion process maintained constantly even if the number of recycle times increased, by putting the fructose raffinate obtained in the psicose preparation process into the fructose preparation process.

Example 2. Production of Fructose Using Fructose Raffinate

The present experiment was carried out to confirm the difference of saccharide composition and yield according to presence/absence of recycling of fructose raffinate.

Specifically, in the fructose preparation process, after mixing corn starch with water to be 30 to 35% by weight, enzymatic hydrolysis was progressed to collect saccharifiprocess consisting of strongly acidic resin, weakly basic resin and strongly acidic and weakly basic mixed resin. That is, by adjusting the total solid content of fructose isomerization product and fructose raffinate put into the primary ion purification process to 50% by weight (50 Brix), the mixture ratio of the fructose isomerization product and fructose raffinate of Preparative Example 2 was 8:2 to 9:1 of weight ratio. After the mixed fructose syrup massed through the primary ion purification and was concentrated to the total solid 50% by weight, it passed through the SMB chromatography process. The glucose raffinate and fructose fraction were obtained by performing the SMB process. The saccharide composition of mixture and raffinate by each process was analyzed and shown in the following Table 2.

TABLE 2

| | Classification | Saccharides over disccharide | Glucose | Fructose | Psicose | Reducing sugar | Solid separation yield |
|---|---|---|---|---|---|---|---|
| No cycle | Fructose isomerization reactant | 2.6% | 54.5% | 42.3% | 0.0% | 0.6% | — |
| | Fructose fraction after SMB separation | 0.3% | 10.4% | 88.0% | 0.0% | 1.2% | 48.1% |
| | Glucose raffinate after SMB separation | 4.7% | 95.3% | 0.0% | 0.0% | 0.0% | 51.9% |
| With cycle | Mixture of fructose isomerization reactant and fructose raffinate | 2.6% | 54.5% | 48.8% | 0.0% | 0.6% | — |
| | Fructose fraction after high purity separation | 0.4% | 10.0% | 88.5% | 0.0% | 1.1% | 55.4% |

TABLE 2-continued

| Classification | Saccharides over disccharide | Glucose | Fructose | Psicose | Reducing sugar | Solid separation yield |
|---|---|---|---|---|---|---|
| Glucose raffinate after high purity separation | 4.7% | 95.3% | 0.0% | 0.0% | 0.0% | 44.6% |

In the Table 2, based on that the total solid content of fructose isomerization reactant, fructose fraction after SMB separation, glucose raffinate after SMB separation, and the mixture of fructose isomerization reactant and fructose raffinate was 100% by weight, the solid content of each composition component was shown as % by weight. The separation yield was shown as the total solid content of fructose fraction after SMB separation (% by weight) and the total solid content of glucose raffinate (% by weight), based on the total solid 100% by weight of feed materials provided in the SMB separation process.

As can be seen in the Table 2, when the fructose separation process was carried out by mixing the raffinate fraction of psicose conversion process with the fructose isomerization reactant of fructose preparation process, based on the total solid 100% by weight of feed materials provided in the SMB separation process, the total solid content of fructose fraction after SMB separation of 48.1% by weight and the glucose raffinate of 51.9% by weight were separated. When mixing the fructose raffinate according to the present invention, the total solid of fructose fraction after SMB separation of 55.4% by weight and the glucose raffinate of 44.6% by weight were separated.

Thus, it was demonstrated that when putting the fructose raffinate of psicose preparation into the separation process of fructose preparation, the fructose content in fructose fraction obtained in the SMB process was increased, and in addition, the solid separation yield was increased by 115%. Therefore, equal fructose purity and yield increasing effect was demonstrated even if mixing the fructose raffinate fraction obtained in the high purity chromatography of psicose preparation process with products which passed through the fructose isomerization process and separating it.

Example 3. Production of Psicose Using Raffinate

The psicose isomerization process and separation process were carried out with the same method as Example 1, but at flow rate of 3.8 m³/hr, in order to produce 10 tons of solids of 95% by weight of psicose content using syrup of 95% by weight of fructose content. The psicose content of products which were passed through the psicose conversion process and collected was 21 to 25% by weight, and they passed through the separation process at a concentration of 45 to 50% by weight after ion purification. The raffinate which was generated when separated by using Ca+ type separation resin was generated by 3 m³ per hour.

The process was carried out, repeated 10 times, and the mixture substrate and the composition of saccharides of raffinate by each process were analyzed and shown in the following Table 3.

TABLE 3

| Classification | Saccharides including disaccharides or higher degree of polymerization | Glucose | Fructose | Psicose | Reducing sugar | Psicose yield |
|---|---|---|---|---|---|---|
| F95 raw material | 0.1% | 3.5% | 95.4% | 0.0% | 1.0% | 27.1% |
| Raffinate of psicose conversion reaction | 0.1% | 3.9% | 94.2% | 1.2% | 0.6% | |
| 5th mixture solution | 0.1% | 3.5% | 95.4% | 0.0% | 1.0% | 27.1% |
| 5th raffinate of psicose conversion reaction | 0.1% | 3.9% | 94.0% | 1.2% | 0.6% | |
| 10th mixture solution | 0.1% | 3.5% | 95.4% | 0.0% | 1.0% | 27.1% |
| 10th raffinate of psicose conversion reaction | 0.1% | 3.9% | 94.2% | 1.2% | 0.6% | |

As can be seen in the Table 3, it was demonstrated that the fructose content of raw material put into the psicose conversion process maintained constantly even if the number of recycle times increased, by putting the raffinate fraction of the psicose preparation process into the fructose preparation process.

Example 4. Production of Fructose Using Raffinate

To confirm the difference of saccharide composition and yield according to presence/absence of recycling of fructose raffinate, an experiment was carried out with the substantially same method as Example 2, but by using the raw material of 95% by weight of fructose content, instead of the raw material of 88% by weight of fructose content in Example 2, the psicose conversion reaction was carried out.

The glucose raffinate and fructose fraction were obtained respectively, by performing the SMB process. The saccharide composition of mixture and raffinate by each process was analyzed and shown in the following Table 4.

TABLE 4

| | Classification | Saccharides including disaccharides or higher degree of polymerization | Glucose | Fructose | Psicose | Reducing sugar | Solid separation yield |
|---|---|---|---|---|---|---|---|
| No cycle | Fructose syrup after fructose isomerization process | 2.6% | 54.5% | 42.3% | 0.0% | 0.6% | — |
| | Fructose fraction after SMB separation | 0.0% | 3.2% | 95.4% | 0.0% | 1.4% | 44.3% |
| | Glucose fraction after SMB separation | 4.7% | 95.3% | 0.0% | 0.0% | 0.0% | 55.7% |
| With cycle | Mixture of fructose isomerization reactant and fructose raffinate | 1.9% | 45.3% | 52.1% | 0.0% | 0.7% | — |
| | Fructose fraction after SMB separation | 0.1% | 3.2% | 95.5% | 0.0% | 1.3% | 54.6% |
| | Glucose fraction after SMB separation | 4.2% | 95.8% | 0.0% | 0.0% | 0.0% | 45.4% |

As can be seen in the Table 4, when performing the fructose separation process by mixing the raffinate fraction of psicose conversion process with the fructose isomerization reactant of fructose preparation process, based on that total solid of feed materials provided in the SMB separation process was 100% by weight, The total solid of fructose fraction after SMB separation of 44.3% by weight and the glucose raffinate of 55.7% by weight were separated. When mixing the fructose raffinate according to the present invention, the total solid of fructose fraction after SMB separation of 54.6% by weight and the glucose raffinate of 45.4% by weight were separated. Thus, it was demonstrated that when putting the fructose raffinate of psicose preparation into the separation process of fructose preparation, the fructose content in fructose fraction obtained in the SMB process was increased, and in addition, the solid separation yield was increased by 123%. Therefore, equal fructose purity and yield increasing effect was demonstrated even if mixing the fructose raffinate fraction obtained in the high purity chromatography of psicose preparation process with products which passed through the fructose isomerization process and separating it.

Example 5. Comparative Experiment of Psicose Conversion Ratio According to Mixed Metal Ion The psicose conversion ratio in the composition similar to the fructose raffinate obtained in the psicose preparation process was evaluated. That is, the psicose conversion process was confirmed by diluting the syrup of fructose purity 95% by weight syrup to 50% by weight and adding $Ca^{2+}$ ion by 0.005~0.01 mM, and then additionally adding 1.0 mM of Mn, and shown in Table 5.

TABLE 5

| Ca ion concentration | Mn ion concentration | Relative activity compared to non-additive control group (%) |
|---|---|---|
| non-additive | non-additive | 100.00 |
| non-additive | 1.0 mM | 152.0 |

TABLE 5-continued

| Ca ion concentration | Mn ion concentration | Relative activity compared to non-additive control group (%) |
|---|---|---|
| 0.005 mM | 1.0 mM | 141.2 |
| 0.008 mM | 1.0 mM | 136.5 |
| 0.010 mM | 1.0 mM | 127.1 |

It was demonstrated that the relative activity of 152% of under the treatment of manganese increasing the activity of psicose conversion reaction, was reduced by about 16% at the maximum when the addition of calcium. The relative activity tended to be reduced gradually as the concentration of calcium ion was increased.

This result shows why it is necessary to purify Ca ion of 0.01 mM or lower precipitated in the separation chromatography process, in reusing the fructose raffinate obtained in the high purity separation chromatography process. In case of no ion purification of fructose raffinate, the activity is lower than the case of using only manganese, thereby negatively affecting the yield of psicose.

The invention claimed is:

1. A method of preparation for psicose comprising:
   separating psicose-conversion product with a simulated moving bed (SMB) chromatography to obtain a psicose fraction and a fructose raffinate,
   providing the fructose raffinate into a separation process of fructose preparation to prepare fructose-containing raw material, and
   conducting psicose conversion reaction by using the fructose-containing raw material,
   wherein the psicose conversion product are obtained by a biological psicose conversion process on fructose raw material using a biocatalyst having a conversion activity from fructose to psicose, and
   wherein the separation process of fructose preparation comprises an ion purification step which removes ion from fructose isomerization product, and a separation step using a SMB chromatography, and the fructose raffinate is provided to one or more kinds of steps selected from the group consisting of the ion purification step and the separation step using SMB chromatography.

2. The method of preparation of claim 1, wherein the separation process of fructose preparation comprises a primary ion purification step which removes ion from fructose isomerization product, a separation step using a SMB chromatography, a secondary ion purification step and a concentration step, and the fructose raffinate is provided to one or more kinds of steps selected from the group consisting of the primary ion purification step, the high purity separation step using the SMB chromatography and the secondary ion purification step.

3. The method of preparation of claim 1, wherein the fructose-containing raw material has an electrical conductivity of 0 to 15 μs/cm.

4. The method of preparation of claim 1, wherein the fructose-containing raw material has a calcium ion concentration of 0.05 mM or lower.

5. The method of preparation of claim 1, wherein the fructose raffinate obtained in the separating step with using the SMB chromatography has an electrical conductivity of 20 to 200 μs/cm.

6. The method of preparation of claim 1, wherein 65 to 95% by weight of a fructose solution obtained in the fructose preparation is mixed with 5 to 35% by weight of the fructose raffinate based on the total 100% by weight of the fructose solution and the fructose raffinate, when the fructose solution and the fructose raffinate are adjusted to 50 Brix each.

7. The method of preparation of claim 1, wherein the fructose content of fructose-containing raw material which is put into the psicose conversion reaction is 85% by weight or higher based on 100% by weight of the total saccharides content.

8. The method of preparation of claim 1, wherein the fructose raffinate obtained in the separating step with the SMB chromatography comprises 85 to 99% by weight of fructose and 2.0% by weight or lower of psicose based on 100% by weight of the total saccharides.

9. The method of preparation of claim 1, wherein the separating step with SMB chromatography process is carried out with a column chromatograph packed with cation exchange resin in which a calcium active group is attached.

10. The method of preparation of claim 1, wherein the psicose conversion reaction uses a biological catalyst having a psicose coversion ratio of 15% to 70%.

11. The method of preparation of claim 1, further comprising a step of cooling the fructose raffinate obtained in the separating step with the SMB chromatography by a heat exchanger.

12. The method of preparation of claim 1, further comprising a step of concentrating the psicose fraction and crystallizing psicose from the concentrates to obtain psicose crystal and crystallization mother liquor.

* * * * *